US006409669B1

(12) United States Patent
Hager et al.

(10) Patent No.: US 6,409,669 B1
(45) Date of Patent: Jun. 25, 2002

(54) ULTRASOUND TRANSDUCER ASSEMBLY INCORPORATING ACOUSTIC MIRROR

(75) Inventors: Richard A Hager, Derry; David W Clark, Windham, both of NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/256,848

(22) Filed: Feb. 24, 1999

(51) Int. Cl.$^7$ ................................................ A61B 8/00
(52) U.S. Cl. ........................ 600/447; 600/445; 128/916
(58) Field of Search ................................. 600/443, 447, 600/459, 445, 446; 128/916; 384/254–275; 73/611, 614

(56) References Cited

U.S. PATENT DOCUMENTS

| | | | | |
|---|---|---|---|---|
| 3,693,414 A | * | 9/1972 | Soldner | 73/614 |
| 4,047,520 A | * | 9/1977 | Soldner et al. | 600/445 |
| 4,128,012 A | * | 12/1978 | Soldner | 73/611 |
| 4,137,777 A | * | 2/1979 | Haverl et al. | 600/445 |
| 4,177,679 A | * | 12/1979 | Soldner | 600/446 |
| 4,208,602 A | * | 6/1980 | Stoller | 600/445 |
| 4,275,597 A | * | 6/1981 | Quedens et al. | 600/445 |
| 4,277,712 A | | 7/1981 | Hanafy | 310/334 |
| 5,027,820 A | | 7/1991 | Pesque | 128/660.07 |
| 5,159,931 A | | 11/1992 | Pini | 128/660.07 |
| 5,229,933 A | | 7/1993 | Larson, III | 364/413.25 |
| 5,267,221 A | | 11/1993 | Miller et al. | 367/140 |
| 5,329,498 A | | 7/1994 | Greenstein | 367/155 |
| 5,435,313 A | | 7/1995 | Noda et al. | 128/662.03 |
| 5,460,181 A | | 10/1995 | Seyed-Bolorforosh | 128/661.01 |
| 5,462,057 A | | 10/1995 | Hunt et al. | |
| 5,488,952 A | * | 2/1996 | Schoolman | 600/443 |
| 5,573,001 A | | 11/1996 | Petrofsky et al. | 128/661.01 |
| 5,575,290 A | | 11/1996 | Teo et al. | 128/661.1 |
| 5,590,658 A | | 1/1997 | Chiange et al. | 128/661.01 |
| 5,622,177 A | | 4/1997 | Breimesser et al. | 128/662.06 |
| 5,655,536 A | | 8/1997 | Takamizawa | 128/661.01 |
| 5,671,746 A | | 9/1997 | Dreschel et al. | 128/661.01 |
| 5,690,114 A | | 11/1997 | Chiange et al. | 128/661.01 |
| 5,732,706 A | | 3/1998 | White et al. | 128/661.01 |
| 5,744,898 A | | 4/1998 | Smith et al. | 310/334 |
| 5,797,845 A | | 8/1998 | Barabash et al. | 600/443 |

OTHER PUBLICATIONS

T. Ota, "Accuracy of Left Ventricular Stroke Volume Measurement Using Real–Time, Three Dimensional Echocardiography Flow Probe in Vivo", 70th Scientific Session Amer. Heart Assn. Meeting, Nov. 11, 1997.

Goldberg, Ri.L. et al, "Multilayer Piezoelectric Ceramics for Two–Dimensional Array Transducers", IEEE Transactions on Ultrasonics, Ferroelectrics & Freq. Control, vol. 41, No. 5, Sep. 1994, pp. 761–771.

(List continued on next page.)

Primary Examiner—Marvin M. Lateef
Assistant Examiner—Ali M. Imam

(57) ABSTRACT

An ultrasound transducer assembly includes an acoustic mirror, an ultrasound transducer positioned to direct a scanned ultrasound beam at the acoustic mirror, wherein the scanned ultrasound beam is reflected by the acoustic mirror to form a reflected ultrasound beam, and an actuating device for moving the acoustic mirror relative to the scanned ultrasound beam so that the reflected ultrasound beam scans a three-dimensional volume. An ultrasound matching fluid may be disposed between the ultrasound transducer and the acoustic mirror. The actuating device may be configured for rotating the acoustic mirror, translating the acoustic mirror or rotating and translating the acoustic mirror. The acoustic mirror may have a single acoustically-reflecting surface of may be a polygon having a plurality of acoustically-reflective surfaces.

24 Claims, 5 Drawing Sheets

OTHER PUBLICATIONS

Takahiro Ota et al, Novel Determination of Left Ventricular, vol. by Tracing Arbitrary Planes Using Real–Time, 3D Echocardiography: In Vitro and In Vivo Validation, 709th Scientific Session American Heart Assn. Meeting, Nov. 11, 1997, pp. 1832.

Fleishman, C. E. et al, "Evaluation of Atrioventricular Valve Abnormalities Using Real–Time Three Dimensional Echocardiography", 70th Scientific Session Amer. Heart Assn. Meeting, Nov. 11, 1997, p. 1045.

Ming Shu et al, "Tricuspid Velocity Profiles Reflect Right Ventricular Diastolic Wall Motion Abnormalities: Real–Time 3D Echocardiography and Computational Fluid Dynamics", 70th Scientific Session Amer. Heart Assn. Meeting, Nov. 11, 1997, p. 2990.

Takahiro S. et al, "Application of a New Real–Time Three–Dimensional Method for Evaluating Right Ventricular Stroke Volume", 70th Scientific Session Amer. Heart Assn. Meeting, Nov. 11, 1997, p. 1830.

S. Smith et al, "Two–Dimensional Array Transducers Using Hybrid Connection Technology", IEEE, Oct. 1992, pp. 555–558, vol. 1.

L. Daane et al, "A demountable Interconnect System for a 50x50 Ultrasonic Imaging Transducer Array", IEEE, Sep. 1997, pp. 978–982.

S. Smith et al, "2–D Array Transducers for Medical Ultrasound at Duke University: 1996", ISAF '96 Proceedings of the 10th IEEE Int'l. Symposium on Appl. of Ferroelectrics, vol. 1, Aug. 1996, pp. 5–11.

R. Goldberg et al, "Multilayer 2–D Array Transducers with Integrated Circuit Transmitters and Receivers: A Feasibility Study", IEEE, 1994 Ultrasonics Symposium, pp. 1511–1514.

A. L. Robinson et al, "Applications of Microelectronics and Micro–fabricaton to Ultrasound Imaging Systems", IEEE 1992, Ultrasonics Symposium Proceedings, vol. 1, pp. 681–691.

* cited by examiner

ULTRASOUND TRANSDUCER ASSEMBLY INCORPORATING ACOUSTIC MIRROR

FIELD OF THE INVENTION

This invention relates to medical ultrasound imaging and, more particularly, to ultrasound transducer assemblies that incorporate acoustic mirrors for three-dimensional ultrasound imaging.

BACKGROUND OF THE INVENTION

Medical ultrasound imaging systems typically use a one-dimensional phased array to form an image of a two-dimensional slice through a patient's body. This approach has limitations. First, the two-dimensional slice is always perpendicular to the face of the transducer, thereby limiting the choice of views. For example, a cardiologist sometimes wants to view heart valves in plane. This requires a double oblique imaging plane with respect to the face of the transducer. This plane can only be derived from three-dimensional data. Second, anatomy such as the left ventricle is inherently three-dimensional. To obtain an accurate volume measurement of the left ventricle, three-dimensional data must be acquired.

Current methods used to acquire three-dimensional data, such as maybe obtained using Hewlett-Packard's Omni Plane transducers, use a one-dimensional array that is mechanically moved in a second dimension. This method may require several minutes to obtain a three-dimensional data set. Furthermore, the organs of interest may move during acquisition of the three-dimensional data set.

Phased array ultrasound transducers having multiple elements in the azimuth direction and a few elements in the elevation direction permit scanning in the azimuth direction and elevation focusing. See for example, U.S. Pat. No. 5,462,057 issued Oct. 31, 1995 to Hunt et al. These transducer configurations, often referred to as 1.5 dimensional arrays, do not permit beam steering in the elevation direction.

Planar, two-dimensional transducer arrays may be used for three-dimensional ultrasound imaging. However, in order to obtain good resolution and large steering angle, a large number of extremely small transducer elements is required. Such transducer arrays are difficult to fabricate and are difficult to interconnect to the imaging system electronics.

A system capable of acquiring real-time, three-dimensional data by electronically steering in two dimensions is described by T. Ota in "Accuracy of Left Ventricular Stroke Volume Measurement Using Real-Time, Three Dimensional Echocardiography Flow Probe in Vivo", 70th Scientific Session American Heart Association Meeting, Nov. 11, 1997. This system uses 512 active transducer elements. Signals from the transducer elements are passed through a cable having 512 coaxial conductors into a system with appropriate electronics. The image quality of the system is limited due to the small number of transducer elements used. Furthermore, since the cable between the transducer and the system has a significant diameter, it is difficult to extend this technology to many more transducer elements without an unacceptably large cable or a cable with such small diameter conductors that significant signal loss will occur.

A device for three-dimensional focusing of an ultrasonic beam is disclosed in U.S. Pat. No. 5,027,820, issued Jul. 2, 1991, to Pesque. The device includes a cylindrical phased array. An acoustic beam may be created by phasing the elements of a selected circumferential segment along the length of the cylindrical array. Although the element count is reduced in comparison with a planar array, the sampling in the circumferential direction is much coarser than the sampling in the lateral direction and provides an irregular data set. A drawback of the cylindrical array is that a large number of elements is still needed along the length of the transducer to achieve an acceptable field of view.

None of the known prior art ultrasound imaging techniques have achieved high quality, high resolution, three-dimensional ultrasound imaging with transducer assemblies that are practical in size, cost and complexity.

SUMMARY OF THE INVENTION

According to a first aspect of the invention, an ultrasound transducer assembly is provided. The transducer assembly comprises an acoustic mirror, an ultrasound transducer positioned to direct a scanned ultrasound beam at the acoustic mirror, wherein the scanned ultrasound beam is reflected by the acoustic mirror to form a reflected ultrasound beam, and an actuating device for moving the acoustic mirror relative to the scanned ultrasound beam so that the reflected ultrasound beam scans a three-dimensional volume.

The transducer assembly preferably further comprises an ultrasound matching fluid disposed between the ultrasound transducer and the acoustic mirror, and an enclosure containing the fluid. The enclosure may include one or more windows for transmitting and receiving ultrasound energy.

In one embodiment, the actuating device for moving the acoustic mirror comprises a motor for producing reciprocating rotational motion of the acoustic mirror. In another embodiment, the acoustic mirror comprises a polygon having a plurality of acoustically-reflective faces, and the actuating device comprises a motor for rotating the polygon. The actuating device may produce stepped movement of the acoustic mirror or continuous movement of the acoustic mirror during scanning of the three-dimensional volume. The actuating device may be configured for rotating the acoustic mirror, translating the acoustic mirror or for rotating and translating the acoustic mirror. The actuating device may be configured for translating and rotating the acoustic mirror so as to produce a three-dimensional scan pattern having an apex that is spaced from the acoustic mirror.

According to another aspect of the invention, apparatus is provided for coupling to and use with an ultrasound transducer. The apparatus comprises an acoustic mirror, an actuating device for moving the acoustic mirror, an ultrasound matching fluid disposed between the ultrasound transducer and the acoustic mirror, and an enclosure containing the fluid. A scanned ultrasound beam produced by the ultrasound transducer is reflected by the acoustic mirror to form a reflected ultrasound beam. The acoustic mirror is moved relative to the scanned ultrasound beam so that the reflected ultrasound beam scans a three-dimensional volume.

According to a further aspect of the invention, a method is provided for ultrasound scanning with an ultrasound transducer. The method comprises the steps of scanning an ultrasound beam with the ultrasound transducer, directing the scanned ultrasound beam at an acoustic mirror, wherein the scanned ultrasound beam is reflected by the acoustic mirror to form a reflected ultrasound beam, and moving the acoustic mirror relative to the scanned ultrasound beam so that the reflected ultrasound beam scans a three-dimensional volume.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
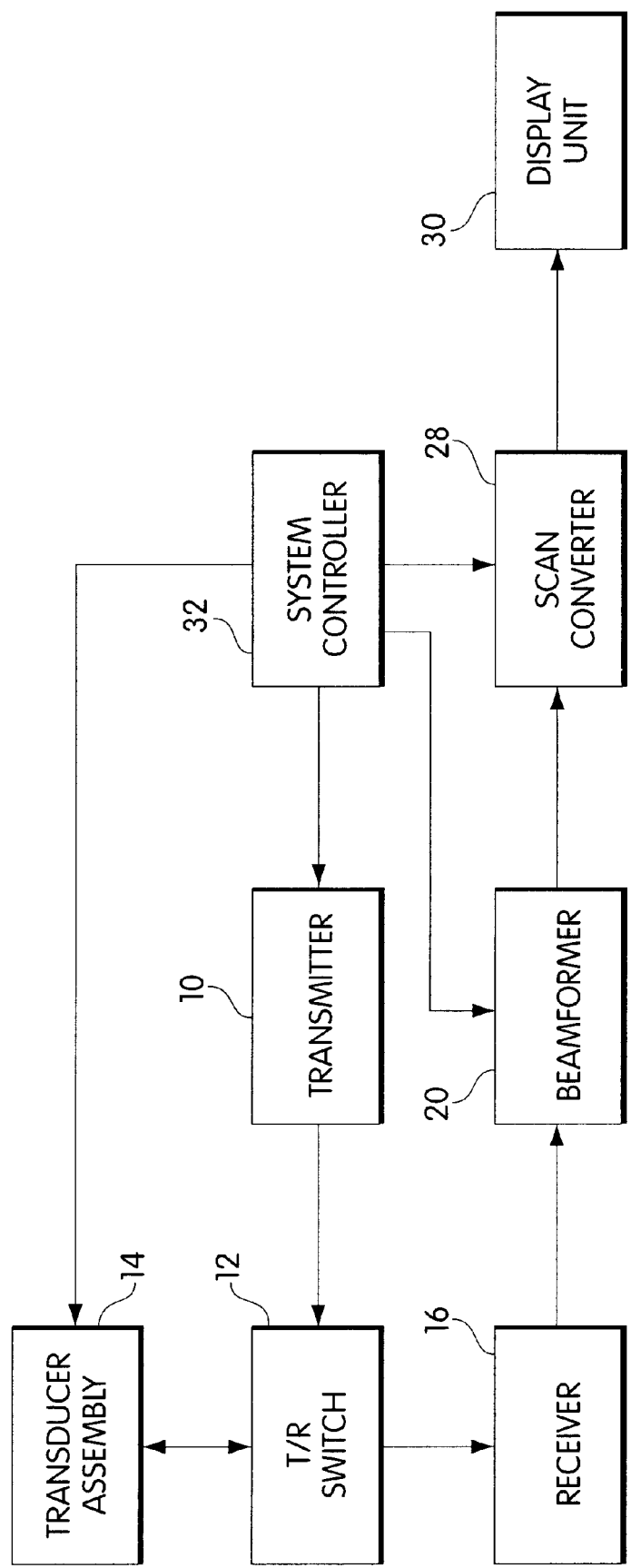
FIG. 1 is a block diagram of an example of an ultrasound imaging system incorporating an ultrasound transducer assembly in accordance with the invention.

A simplified block diagram of an example of an ultrasound imaging system is shown in FIG. 1. A transmitter 10 is coupled through a transmit/receive (T/R) switch 12, having one switch element for each transducer element, to an ultrasound transducer assembly 14. The transducer assembly transmits ultrasound energy into a region of interest in a patient's body and receives reflected ultrasound energy, or echoes, from various structures and organs within the patient's body. The transducer assembly 14 includes an array of transducer elements. As is known in the art, by appropriately delaying the pulses applied to each transducer element by transmitter 10, a focused ultrasound beam is transmitted along a desired scan line. The transducer assembly 14 is configured as described in detail below to permit three-dimensional ultrasound imaging.

The transducer assembly 14 is coupled through T/R switch 12 to an ultrasound receiver 16. Ultrasound energy from a given point within the patient's body is received by the transducer elements at different times. The transducer elements convert the received ultrasound energy to transducer signals which are amplified by receiver 16 and are supplied to a receive beamformer 20. The signals from each transducer element are individually delayed and then are summed by the beamformer 20 to provide a beamformer signal that represents the received ultrasound level along a desired scan line. As known in the art, the delays applied to the transducer signals may be varied during reception of ultrasound energy to effect dynamic focusing. The process is repeated for multiple scan lines to provide signals for generating an image of a region of interest in the patient's body.

In an alternative system configuration, different transducer elements are used for transmit and receive. In that configuration, the T/R switch 12 is not required, and the transmitter 10 and the receiver 16 are connected directly to the respective transmit and receive transducer elements.

A scan converter 28 converts beamformer signals generated by beamformer 20 to conventional raster display signals. The output of scan converter 28 is supplied to a video display unit 30, which displays an image of the region of interest in the patient's body. A system controller 32 provides overall control of the system. The system controller 32 performs timing and control functions and typically includes a microprocessor and associated memory.

Figure 2:
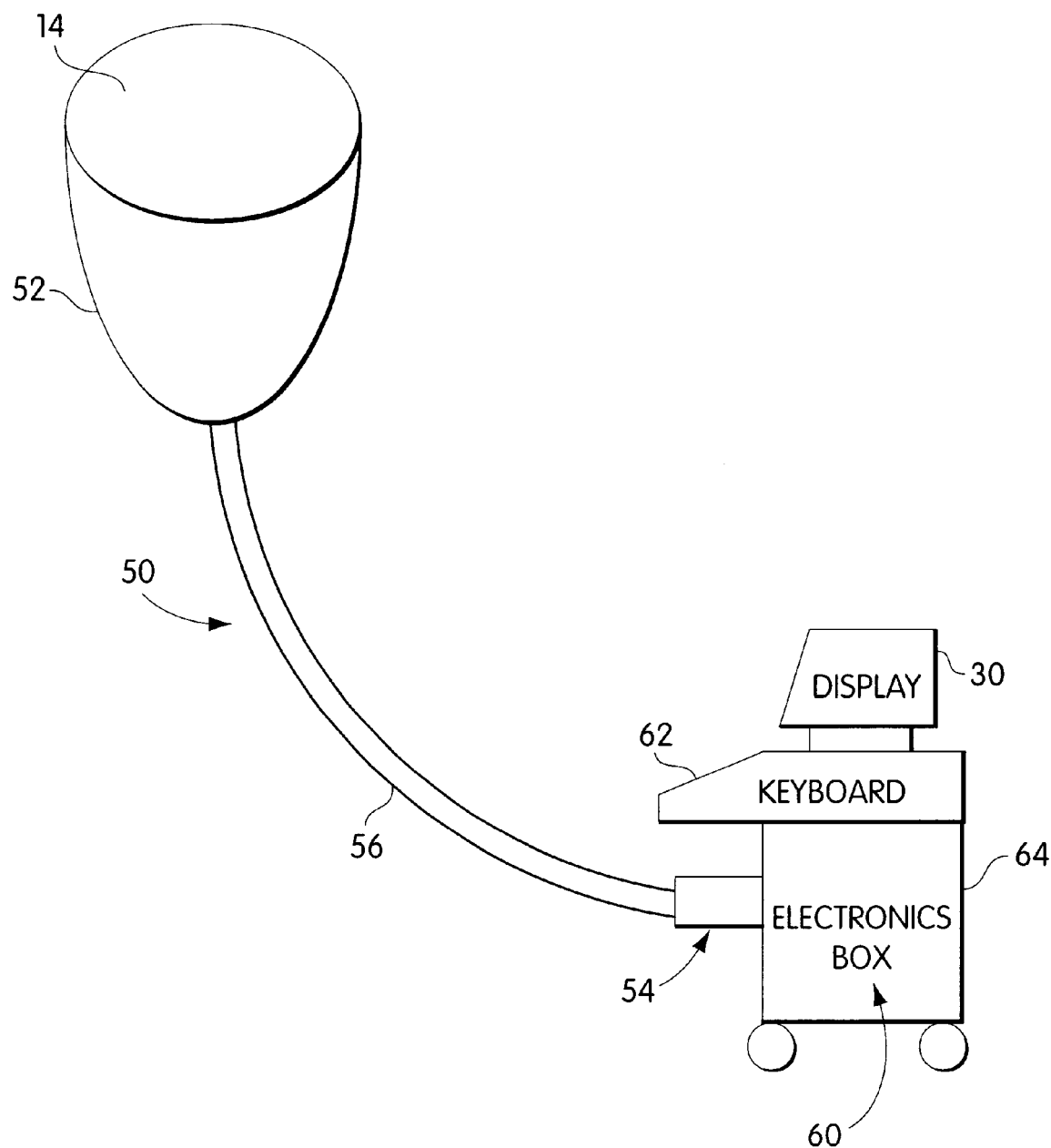
FIG. 2 is a pictorial view of an example of an ultrasound imaging system.

A pictorial view of an example of an ultrasound imaging system incorporating the present invention is shown in FIG. 2. A transducer unit 50 (not shown to scale) includes a transducer handle, or head 52, a transducer connector 54 and a cable 56 interconnecting handle 52 and connector 54. The transducer unit 50 is attached by connector 54 to an electronics console 60, which may include display unit 30, a keyboard 62 and an electronics box 64. The transducer handle 52 includes transducer assembly 14 and may include electronic circuitry.

Figure 3:
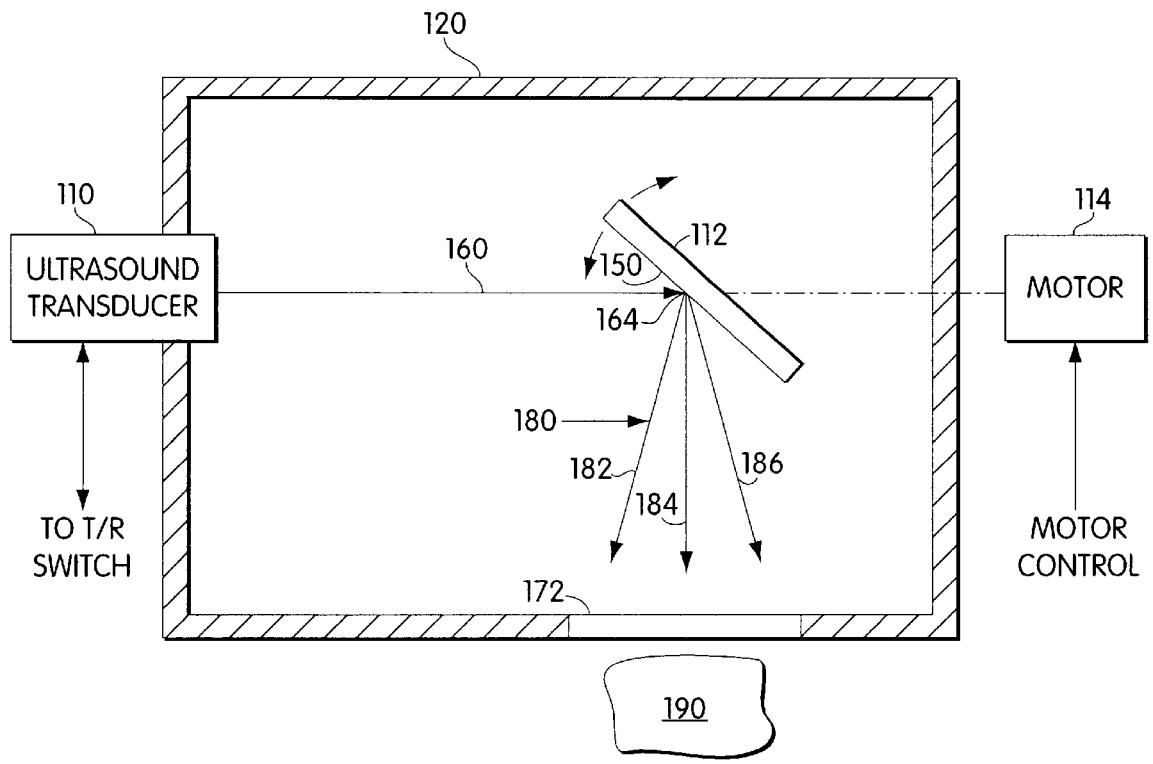
FIG. 3 is a schematic side view of a first embodiment of an ultrasound transducer assembly in accordance with the present invention.
Figure 4:
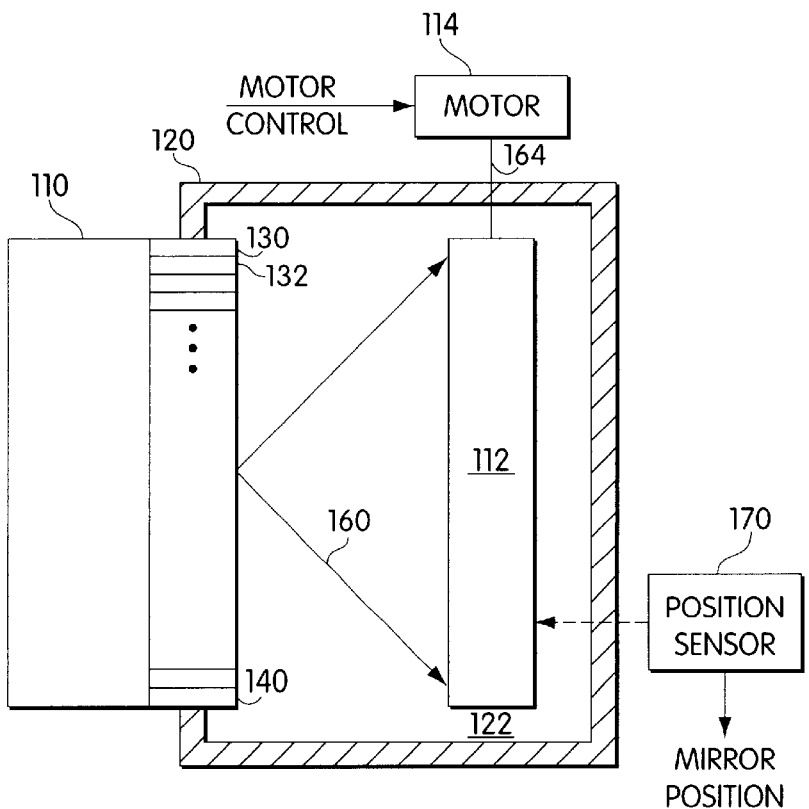
FIG. 4 is a schematic top view of the ultrasound transducer assembly of FIG. 3.

A first embodiment of an ultrasound transducer assembly in accordance with the invention is shown in FIGS. 3 and 4. FIG. 3 is a side schematic view, and FIG. 4 is a top schematic view of the transducer assembly. The transducer assembly includes an ultrasound transducer 110, an acoustic mirror 112, an actuating device, such as a motor 114, for moving acoustic mirror 112, and an enclosure 120 containing an ultrasound matching fluid 122. The ultrasound transducer 110 may include an array of transducer elements 130, 132, ... 140 such as is used for phased array ultrasound imaging. A typical array may include 128 transducer elements. Techniques for fabrication of transducer arrays are well known to those skilled in the art.

Acoustic mirror 112 has an acoustically-reflecting surface 150 that is fabricated of a material having a significantly different acoustic impedance from fluid 122 or other medium between transducer 110 and acoustic mirror 112. Suitable materials for reflecting surface 150 of acoustic mirror 112 include steel and other metals, and plastics which have the required acoustic impedance. Preferably, reflecting surface 150 is flat and smooth to provide uniform reflection of ultrasound energy. In other configurations, reflecting surface 150 may have a desired curvature, either convex or concave, to produce focusing or other modification of an incident ultrasound beam. Reflecting surface 150 should have acoustic characteristics which ensure reflection of ultrasound energy over the range of ultrasound frequencies transmitted and received by ultrasound transducer 110.

Acoustic mirror 112 is mounted in the transducer assembly so that reflecting surface 150 intercepts a scanned ultrasound beam 160 transmitted by ultrasound transducer 110. Acoustic mirror 112 is preferably positioned as close to transducer 110 as is practical to permit unrestricted rotation of acoustic mirror 112 and to limit the size of the transducer assembly.

Motor 114 is mechanically coupled to acoustic mirror 112 and produces rotation of acoustic mirror 112 about an axis 164. In the example of FIGS. 3 and 4, axis 164 is located on reflecting surface 150 in the plane of scanned ultrasound beam 160 and is parallel to the transmitting face of ultrasound transducer 110. Acoustic mirror 112 is rotated by motor 114 through a prescribed angular range with reciprocating rotational motion. The angular range depends on the size of the volume to be scanned. The rotation of acoustic mirror 112 by motor 114 is controlled by a motor control signal from system controller 32 (FIG. 1). The rotation of acoustic mirror 112 about axis 164 may be continuous or stepped between the limits of the reciprocating rotational motion.

A position sensor 170 (FIG. 4) may be utilized to sense the position of acoustic mirror 112 and to provide a mirror position signal to system controller 32. Position sensor 170, for example, may be a shaft encoder.

Ultrasound matching fluid 122 provides matching between the ultrasound transducer assembly and the object being imaged, typically the human body. Thus, fluids which have acoustic properties similar to tissue may be utilized. Examples of suitable fluids include methyl salicylate, glycol, mixtures of water and glycol, and the like. Enclosure 120 is configured to surround at least the transmitting and receiving face of ultrasound transducer 110 and acoustic mirror 112. Enclosure 120 is provided with a window 172 for transmitting and receiving ultrasound energy. Window 172 has acoustic properties which limit reflections of ultrasound energy. Suitable window materials include plastics and rubber materials such as certain polyethylene or polyurethane formulations having acoustic properties which match those of human tissue.

In operation, transmitter 10 (FIG. 1) energizes the elements 130, 132, . . . 140 of ultrasound transducer 110 to produce scanned ultrasound beam 160. Scanned ultrasound beam 160 has a two-dimensional scan pattern, such as a sector scan pattern or a parallel scan pattern. Techniques for generating such scan patterns are known in the art. Acoustic mirror 112 is positioned to intercept scanned ultrasound beam 160. Reflecting surface 150 of acoustic mirror 112 reflects scanned ultrasound beam 160 to produce a reflected ultrasound beam 180.

The rotation of acoustic mirror 112 about axis 164 causes scanned ultrasound beam 160 to be reflected in different directions to thereby scan a three-dimensional volume. Preferably, the rotation rate of acoustic mirror 112 is slow in comparison with the scanning rate of scanned ultrasound beam 160. For example, when stepped rotation of acoustic mirror 112 is utilized, acoustic mirror 112 may be rotated to a new position following each complete scan of ultrasound beam 160. In this instance, reflected ultrasound beam 180 includes multiple two-dimensional slices 182, 184, 186, etc. The sizes of the steps determine the spacing between the two-dimensional slices. When continuous movement of acoustic mirror 112 is utilized, the rotation rate of acoustic mirror 112 is selected to provide a desired scan line density.

The electronic scanning of ultrasound beam 160 combined with the rotation of acoustic mirror 112 produces reflected ultrasound beam 180, which scans a three-dimensional volume. Reflected ultrasound beam 180 passes through window 172 into a region of interest 190 in a patient. Ultrasound echos from region of interest 190 pass through window 172 and are reflected by acoustic mirror 112 to ultrasound transducer 110. The ultrasound echos are converted by the elements 130, 132, . . . 140 of ultrasound transducer 110 to electrical signals which are processed by the imaging system shown in FIG. 1 to produce an image of the region of interest 190.

Figure 5:
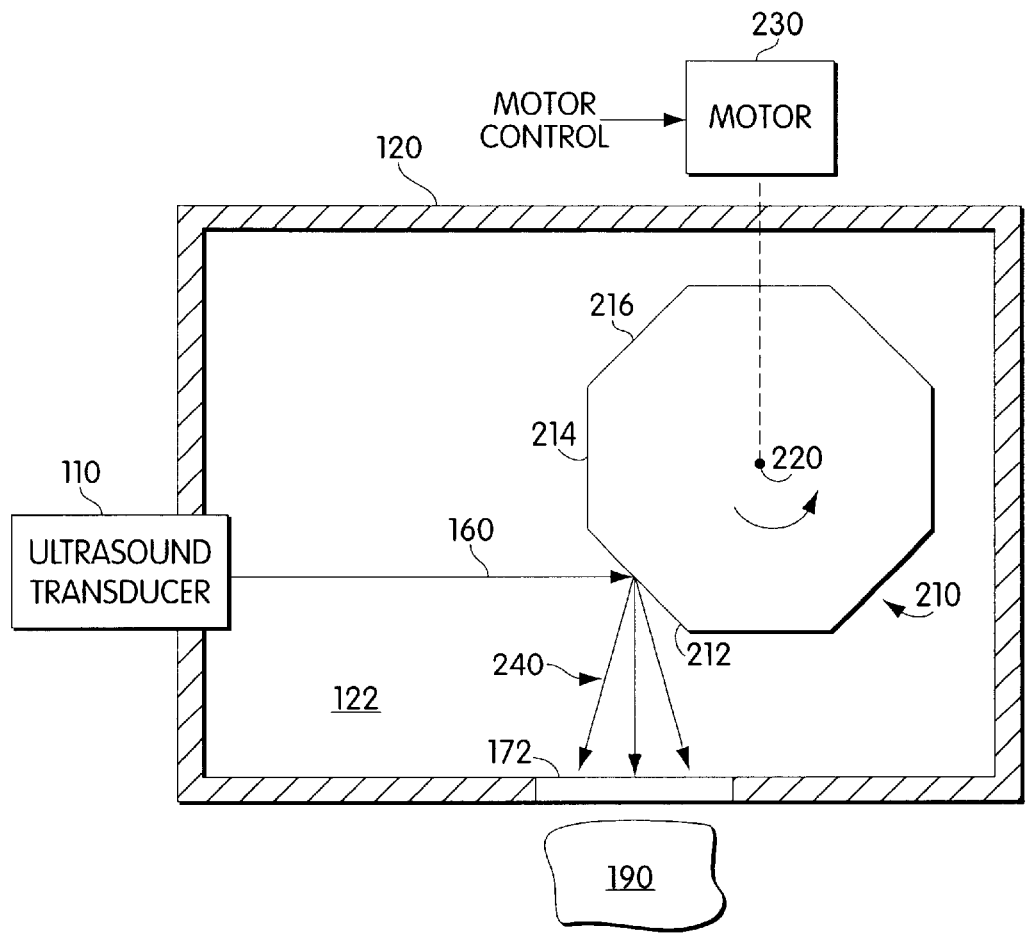
FIG. 5 is a schematic side view of a second embodiment of an ultrasound transducer assembly in accordance with the invention.

A second embodiment of an ultrasound transducer assembly in accordance with the invention is shown in FIG. 5. Like elements in FIGS. 3–5 have the same reference numerals. An acoustic mirror 210 is configured as a polygon having a plurality of acoustically-reflecting surfaces 212, 214, 216, etc. Acoustic mirror 210 is mounted for rotation about an axis 220 so that reflecting surfaces 212, 214, 216, etc. are successively brought into alignment with scanned ultrasound beam 160. Acoustic mirror 210 is mechanically coupled to an actuating device, such as a motor 230, which produces rotation in one direction, rather than reciprocating motion, in response to a motor control signal. Each reflecting surface changes angle with respect to scanned ultrasound beam 160 as it rotates about axis 220, so that a reflected ultrasound beam 240 scans a three-dimensional volume. Acoustic mirror 210 rotates about axis 220 at an angular speed which is selected to permit a three-dimensional volume to be scanned with each reflecting surface. As in the embodiment of FIGS. 3 and 4, rotation of acoustic mirror 210 about axis 220 may be continuous or stepped.

Figure 6:
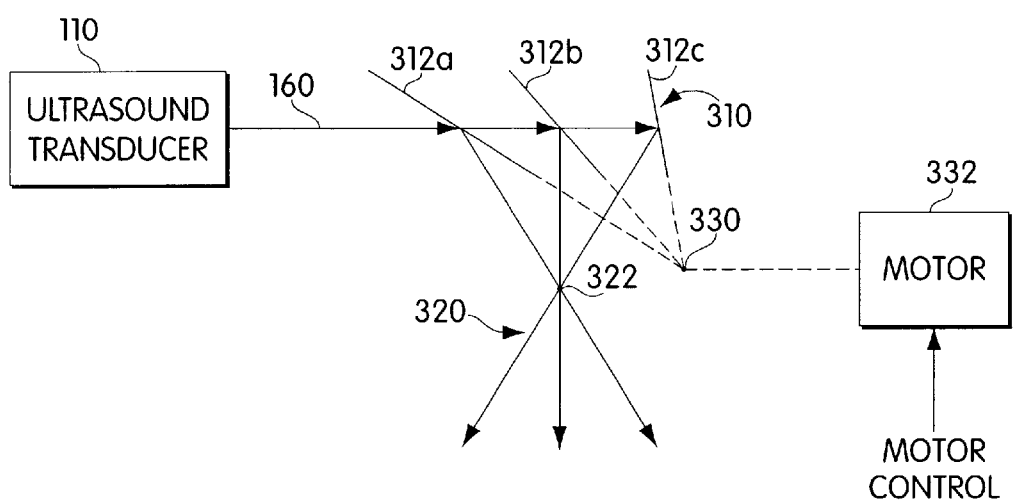
FIG. 6 is a schematic side view of a third embodiment of an ultrasound transducer assembly in accordance with the invention.

A third embodiment of an ultrasound transducer assembly in accordance with the invention is shown in FIG. 6. The fluid and the fluid enclosure have been omitted from FIG. 6 for ease of illustration. However, it will be understood that the region between the ultrasound transducer and the acoustic mirror is filled with an ultrasound matching fluid. Like elements in FIGS. 3–6 have the same reference numerals. In the embodiment of FIG. 6, an acoustic mirror 310 is rotated and translated simultaneously with respect to scanned ultrasound beam 160 to produce a desired three-dimensional scan pattern. Acoustic mirror 310 is shown in FIG. 6 in positions 312*a*, 312*b* and 312*c*, which are rotated and translated relative to scanned ultrasound beam 160. A reflected ultrasound beam 320 has a three-dimensional pattern with an apex 322 that is spaced from acoustic mirror 310. A scan pattern of this type may be useful, for example, for obtaining so-called "keyhole" images between ribs or other structures. The apex 322 of the scan pattern is positioned between the ribs so that an image can be obtained without blockage by the ribs. It will be understood that different scan patterns can be obtained with different rotational and translational movement of acoustic mirror 310.

In the example of FIG. 6, acoustic mirror 310 may be rotated about an axis 330 by an actuating device, such as a motor 332, in response to a motor control signal to produce combined rotational and translational movements. Axis 330 is displaced from acoustic mirror 310. Separate rotational and translational actuators may be used to provide arbitrarily selected rotational and translational movements of acoustic mirror 310.

Figure 7:
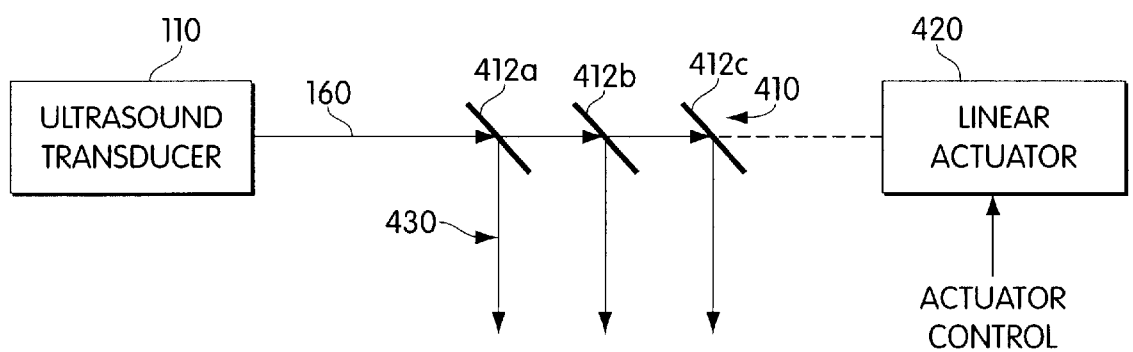
FIG. 7 is a schematic side view of a fourth embodiment of an ultrasound transducer assembly in accordance with the invention.

A fourth embodiment of ultrasound transducer assembly in accordance with the invention is shown in FIG. 7. Like elements in FIGS. 3–7 have the same reference numerals. The ultrasound matching fluid and the fluid enclosure have been omitted from FIG. 7 for ease of illustration. However, it will be understood that a matching fluid is provided between the ultrasound transducer and the acoustic mirror. In the embodiment of FIG. 7, an acoustic mirror 410 is translated to a plurality of positions 412*a*, 412*b*, 412*c* without rotation. A linear actuator 420 coupled to acoustic mirror 410 produces the desired translation in response to an actuator control signal. A reflected ultrasound beam 430 scans a three-dimensional volume that is determined in part by the translation distance of acoustic mirror 410. It will be understood that the translation of acoustic mirror 410 in the embodiments of FIGS. 6 and 7 does not necessarily follow a linear path.

Movement of the acoustic mirror in the ultrasound transducer assembly of the present invention may be continuous or stepped. Continuous movement may be at constant or variable speed. Stepped movement may utilize constant or variable size steps. Furthermore, the movement may be rotational movement, translational movement or a combination of rotational and translational movements. In each case, a scanned ultrasound beam is directed at an acoustic mirror, and the acoustic mirror is moved, so that the reflected ultrasound beam covers a three-dimensional volume. The ultrasound beam may be electronically scanned in azimuth, using, for example, a sector scan pattern or a parallel scan pattern, and the reflected ultrasound beam may be scanned in elevation by movement of the acoustic mirror.

According to another feature of the invention, scanning apparatus may be provided for converting a conventional ultrasound transducer used for two-dimensional scanning into a transducer assembly for three-dimensional scanning. With reference to the embodiments of FIGS. 3–6, an adapter may be provided for mounting the acoustic mirror in spaced relationship to the ultrasound transducer, such that the scanned ultrasound beam produced by the ultrasound transducer is incident upon and is reflected by the acoustic mirror. With reference to FIGS. 3 and 4, the scanning apparatus for use with ultrasound transducer 110 may include enclosure 120, ultrasound matching fluid 122, acoustic mirror 112 and motor 114. Enclosure 120 may include an adapter for attachment to ultrasound transducer 110. In one embodiment, ultrasound transducer 110 may be sealed to an opening in enclosure 120. In another embodiment, enclosure 120 may include a window (not shown) for transmitting ultrasound beam 160. Similar scanning apparatus may be configured for the embodiments of FIGS. 5–7. Such apparatus permit a conventional ultrasound transducer to be utilized for three-dimensional scanning.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An ultrasound transducer assembly comprising:
   an acoustic mirror;
   an ultrasound transducer that linearly scans an ultrasound beam across said acoustic mirror, wherein said scanned ultrasound beam is reflected by said acoustic mirror to form a reflected ultrasound beam that scans along a first direction; and
   an actuating device for moving said acoustic mirror relative to said scanned ultrasound beam so as to adjust the scanning position of said reflected ultrasound beam along a second direction traverse to the first direction to scan a three-dimensional volume.

2. An ultrasound transducer assembly as defined in claim 1 further comprising an ultrasound matching fluid disposed between said ultrasound transducer and said acoustic mirror, and an enclosure containing said fluid.

3. An ultrasound transducer assembly as defined in claim 2 wherein said acoustic mirror is disposed in said fluid.

4. An ultrasound transducer assembly as defined in claim 1 wherein said ultrasound transducer comprises an array of transducer elements.

5. An ultrasound transducer assembly as defined in claim 1 wherein the first direction is along an azimuth and the second direction is along an elevation.

6. An ultrasound transducer assembly as defined in claim 1 further comprising a position sensor for sensing the position of said acoustic mirror.

7. An ultrasound transducer assembly as defined in claim 1 wherein said actuating device comprises a motor for producing reciprocating rotational motion of said acoustic mirror.

8. An ultrasound transducer assembly as defined in claim 1 wherein said acoustic mirror comprises a polygon having a plurality of acoustically-reflective faces and wherein said actuating device comprises a motor for rotating said polygon.

9. An ultrasound transducer assembly as defined in claim 1 wherein said actuating device comprises a motor for producing stepped movement of said acoustic mirror during scanning of said three-dimensional volume.

10. An ultrasound transducer assembly as defined in claim 1 wherein said actuating device comprises a motor for producing continuous movement of said acoustic mirror during scanning of said three-dimensional volume.

11. An ultrasound transducer assembly as defined in claim 1 wherein said actuating device is configured for rotating said acoustic mirror.

12. An ultrasound transducer assembly as defined in claim 1 wherein said actuating device is configured for translating said acoustic mirror.

13. An ultrasound transducer assembly as defined in claim 1 wherein said actuating device is configured for rotating and translating said acoustic mirror.

14. An ultrasound transducer assembly as defined in claim 1 wherein said actuating device is configured for translating and rotating said acoustic mirror so as to produce a three-dimensional scan pattern having an apex that is spaced from said acoustic mirror.

15. Apparatus for coupling to and use with a phased linear array ultrasound transducer, comprising:
   an acoustic mirror mounted in said apparatus such that, when said apparatus is coupled to the ultrasound transducer an ultrasound beam produced by the ultrasound transducer is reflected by said acoustic mirror to form a reflected ultrasound beam scanned in an azimuth direction;
   an actuating device for moving said acoustic mirror relative to the scanned ultrasound beam so as to move said reflected ultrasound beam in an elevation direction thereby scanning a three-dimensional volume;
   an ultrasound matching fluid disposed between the ultrasound transducer and the acoustic mirror; and
   an enclosure containing said fluid.

16. Apparatus as defined in claim 15 wherein said actuating device is configured for rotating said acoustic mirror.

17. Apparatus as defined in claim 15 wherein said actuating device is configured for translating said acoustic mirror.

18. Apparatus as defined in claim 15 wherein said actuating device is configured for rotating and translating said acoustic mirror.

19. A method for ultrasound scanning with an ultrasound transducer, comprising the steps of:
   linearly scanning an ultrasound beam with the ultrasound transducer;
   directing the scanned ultrasound beam at an acoustic mirror, wherein said scanned ultrasound beam is reflected by said acoustic mirror to form a reflected ultrasound beam scanned in a first direction; and
   moving said acoustic mirror relative to said scanned ultrasound beam so that said reflected ultrasound beam is adjusted in a second direction traverse to the first direction, whereby the reflected ultrasound beam scans a three-dimensional volume.

20. A method as defined in claim 19 further comprising the step of disposing an ultrasound matching fluid between the ultrasound transducer and the acoustic mirror.

21. A method as defined in claim 19 wherein the step of moving said acoustic mirror comprises rotating said acoustic mirror.

22. A method as defined in claim 19 wherein the step of moving said acoustic mirror comprises translating said acoustic mirror.

23. A method as defined in claim 19 wherein the step of moving said acoustic mirror comprises rotating and translating said acoustic mirror.

24. A method as defined in claim 19 wherein the step of moving said acoustic mirror comprises translating and rotating said acoustic mirror so as to produce a three-dimensional scan pattern having an apex that is spaced from said acoustic mirror.

* * * * *